United States Patent
Sakai

(10) Patent No.: US 11,445,936 B2
(45) Date of Patent: Sep. 20, 2022

(54) ENDOSCOPIC SYSTEM AND IMAGE DIAGNOSING SYSTEM

(71) Applicant: Olympus Corporation, Hachioji (JP)

(72) Inventor: Yuji Sakai, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 481 days.

(21) Appl. No.: 16/720,680

(22) Filed: Dec. 19, 2019

(65) Prior Publication Data

US 2020/0121218 A1    Apr. 23, 2020

Related U.S. Application Data

(63) Continuation of application No. PCT/JP2017/025254, filed on Jul. 11, 2017.

(51) Int. Cl.
*A61B 5/06* (2006.01)
*A61B 1/00* (2006.01)
*A61B 1/05* (2006.01)

(52) U.S. Cl.
CPC ............ *A61B 5/062* (2013.01); *A61B 1/0005* (2013.01); *A61B 1/00006* (2013.01); *A61B 1/05* (2013.01)

(58) Field of Classification Search
CPC ... A61B 5/062; A61B 1/00006; A61B 1/0005; A61B 1/05
See application file for complete search history.

(56) References Cited

U.S. PATENT DOCUMENTS

| 2011/0125006 A1 | 5/2011 | Yamamoto et al. |
| 2014/0046324 A1 | 2/2014 | Belson et al. |
| 2016/0324399 A1* | 11/2016 | Ban ................ G02B 23/2484 |

(Continued)

FOREIGN PATENT DOCUMENTS

| JP | 2006-314775 A | 11/2006 |
| JP | 2009-201618 A | 9/2009 |

(Continued)

OTHER PUBLICATIONS

International Preliminary Report on Patentability together with the Written Opinion issued in International Application No. PCT/JP2017/025254 dated Jan. 23, 2020.

(Continued)

*Primary Examiner* — Rowina J Cattungal
(74) *Attorney, Agent, or Firm* — Scully, Scott, Murphy & Presser, P.C.

(57) ABSTRACT

The disclosed technology is directed to an endoscopic system comprises an endoscope having a shank and a photodetector engaged with one another and having an optical axis in a direction transverse to the shank. A display device for displaying an image acquired through the photodetector. A first probe is disposed in the endoscope on or around the optical axis at a position off the shank. A second probe is disposed in the endoscope at or near a position where the shank and the optical axis intersect with each other. A sensor for detecting the position of the first probe and the position of the second probe and a controller. The controller is configured to establish a first reference direction in an actual space. To acquire a direction from the second probe toward the first probe and to perform a process for indicating the first reference direction to a user.

13 Claims, 11 Drawing Sheets

(56) References Cited

U.S. PATENT DOCUMENTS

| | | |
|---|---|---|
| 2016/0360951 A1 | 12/2016 | Hane |
| 2017/0035516 A1 | 2/2017 | Tojo et al. |
| 2017/0090181 A1* | 3/2017 | Innami ............... G02B 23/2469 |
| 2017/0172389 A1 | 6/2017 | Fujisaki et al. |
| 2018/0028052 A1* | 2/2018 | Kojo .................. A61B 1/00172 |

FOREIGN PATENT DOCUMENTS

| | | |
|---|---|---|
| JP | 2009-254805 A | 11/2009 |
| JP | 2013-061558 A | 4/2013 |
| JP | 2015-181643 A | 10/2015 |
| JP | 2015-223440 A | 12/2015 |
| JP | 2017-074465 A | 4/2017 |
| JP | 2017-080422 A | 5/2017 |

OTHER PUBLICATIONS

International Search Report dated Oct. 10, 2017 issued in International Application No. PCT/JP2017/025254.

* cited by examiner

ENDOSCOPIC SYSTEM AND IMAGE DIAGNOSING SYSTEM

CROSS-REFERENCE TO RELATED APPLICATION

This application is a continuation application of PCT Application No. PCT/JP2017/025254 filed on Jul. 11, 2017, which is hereby incorporated by reference in its entirety.

TECHNICAL FIELD

The disclosed technology relates to an endoscopic system for carrying out in vivo observations of a medical examinee.

DESCRIPTION OF THE RELATED ART

For example, Japanese Patent Application JP 2006-314775A (PTL 1) discloses an endoscopic device capable of adjusting the bent angle of an insertion portion thereof. The endoscopic device includes a plurality of acceleration sensors that are capable of detecting the bent state of the insertion portion.

Endoscopes that observe the inside of human bodies will prove more useful to the user if they can acquire, with some means, a direction in which the user is seeing with the endoscope. Therefore, there have been demands for an endoscopic system capable of acquiring a direction in which the user is seeing with an endoscope.

BRIEF SUMMARY OF EMBODIMENTS

The disclosed technology is directed to an endoscopic system comprises an endoscope having a shank and a photodetector engaged with one another and having an optical axis in a direction transverse to the shank. A display device for displaying an image acquired through the photodetector. A first probe is disposed in the endoscope on or around the optical axis at a position off the shank. A second probe is disposed in the endoscope at or near a position where the shank and the optical axis intersect with each other. A sensor for detecting the position of the first probe and the position of the second probe and a controller. The controller is configured to establish a first reference direction in an actual space. Next, to acquire a direction from the second probe toward the first probe or a direction from the first probe toward the second probe as a direction of the optical axis. Then, to perform a process for indicating the first reference direction to a user in the image displayed on the display device when an angle formed between the direction of the optical axis and the first reference direction exceeds a predetermined threshold value.

Another aspect of the disclosed technology is directed to an image diagnosing system having an endoscopic system comprises an endoscope having a shank and a photodetector engaged with one another and having an optical axis in a direction transverse to the shank. A display device for displaying an image acquired through the photodetector. A first probe is disposed in the endoscope on or around the optical axis at a position off the shank. A second probe is disposed in the endoscope at or near a position where the shank and the optical axis intersect with each other. A sensor for detecting the position of the first probe and the position of the second probe. A sectional image acquiring device for acquiring at least one sectional image of a medical examinee and a controller. The controller is configured to display a first image acquired by the endoscope and at least one second image acquired by the sectional image acquiring device, in an array on the display device, to establish a first reference direction in an actual space, to acquire a direction from the second probe toward the first probe or a direction from the first probe toward the second probe as a direction of the optical axis, and to perform a process for indicating the first reference direction to a user in the first image displayed on the display device when an angle formed between the direction of the optical axis and the first reference direction exceeds a predetermined threshold value.

A further aspect of the disclosed technology to a method of detecting an observational direction of an endoscope used in an endoscopic system. The method comprises detecting a position of a first probe disposed in the endoscope on or around an optical axis thereof at a position off a shank thereof. Next, detecting a position of a second probe disposed in the endoscope at or near a position where the shank and the optical axis intersect with each other. Then, establishing a first reference direction in an actual space and acquiring a direction from the second probe toward the first probe or a direction from the first probe toward the second probe as a direction of the optical axis. Finally, indicating the first reference direction to a user when an angle formed between the direction of the optical axis and the first reference direction exceeds a predetermined threshold value.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

First Embodiment

A first embodiment of an image diagnosing system and an endoscopic system using the image diagnosing system will be described hereinafter with reference to FIGS. 1 through 11.

Figure 1:
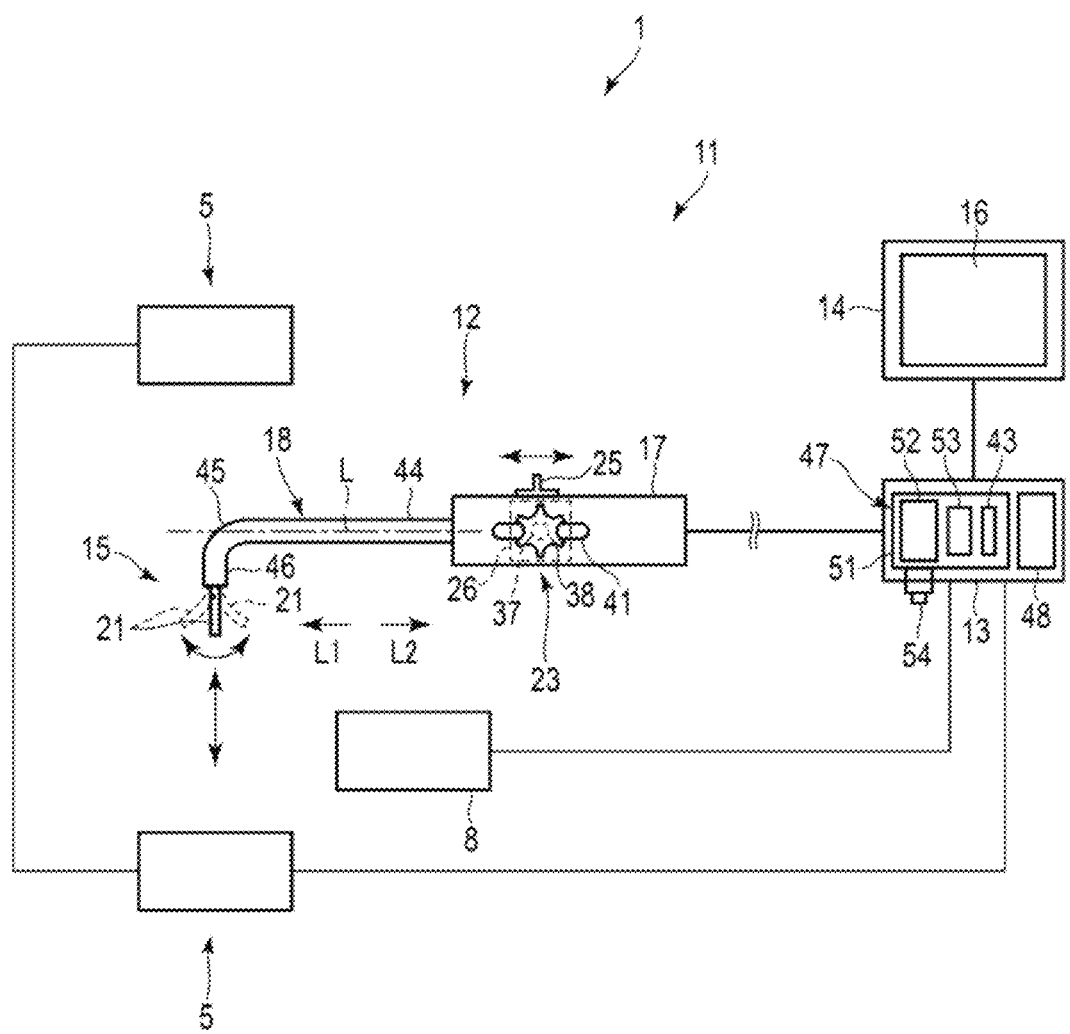
FIG. 1 is a schematic view illustrating the overall makeup of an image diagnosing system and an endoscopic system according to a first embodiment.

As illustrated in FIG. 1, an image diagnosing system 1 has a sectional image acquiring device 5 for acquiring sectional images of a medical examinee and an endoscopic system 11 that is inserted into the body of the medical examinee and used for carrying out in vivo observations of the medical examinee. The sectional image acquiring device 5 may be a CT (Computed Tomography) device, but is not limited to the CT device. The sectional image acquiring device 5 is capable of acquiring, for example, a coronal section image 64, an axial section image 65, and a sagittal section image 66 (see FIG. 4). The sectional image acquiring device 5 may be a device capable of acquiring sectional images other than the CT device, such as an MRI (Magnetic Resonance Imaging) device, for example.

The endoscopic system 11 has an insertion device 12 for being inserted into a nasal cavity, a paranasal cavity, or the like, a controller 13 electrically connected to the insertion device 12 through an electric power line that supplies electric power to the insertion device 12 and various signal lines, a display device 14 connected to the controller 13, and a navigation system 8 for detecting the position and posture of the insertion device 12. The navigation system 8 represents an example of sensor. The navigation system 8 is constructed as a magnetic sensor, for example, capable of magnetically detecting the positions of first through third probes 61 through 63 (see FIG. 3) included in the endoscopic system 11. The navigation system 8 may be an optical sensor for detecting the positions of the first through third probes 61 through 63 with an infrared radiation.

The insertion device 12 is disposed separately from the display device 14 and the controller 13. The display device 14 is a general liquid crystal monitor that can display an image acquired by an endoscope 15 as an image, i.e., an endoscope image, 16.

Figure 2:
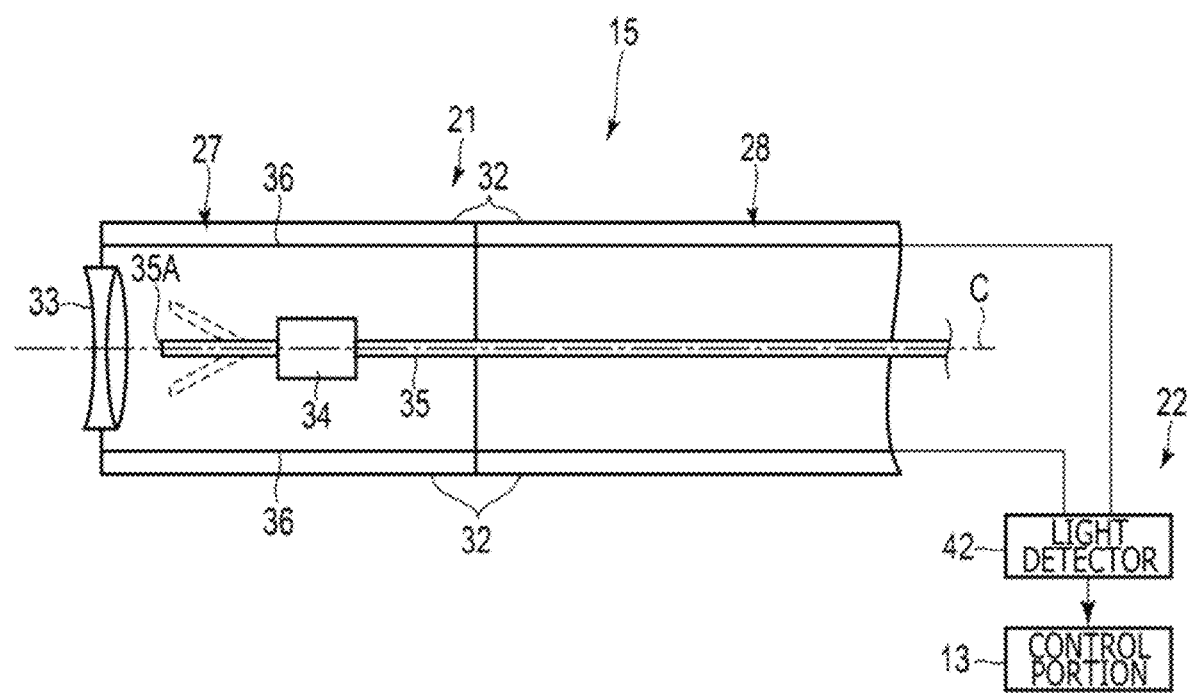
FIG. 2 is a side elevational see-through view illustrating a distal-end structure portion of an endoscope insertion portion of the endoscopic system illustrated in FIG. 1.

As illustrated in FIGS. 1 and 2, the insertion device 12 has a grip portion 17 as an outer shell, a tubular guide pipe 18 projecting from the grip portion 17, a main endoscope body 21 inserted in the guide pipe 18 and the grip portion 17, an endoscope image capturing portion, i.e., image capturing portion, 22 disposed in the grip portion 17, and a bend actuator 23 mounted on the grip portion 17. The grip portion 17 is shaped as a hollow cylinder that functions as a portion, i.e., housing, to be gripped by the hand of the user.

According to the present embodiment, as illustrated in FIG. 2, the endoscope 15 has the main endoscope body 21 and the endoscope image capturing portion 22. The endoscope 15 may be arranged such that the main endoscope body 21 and the endoscope image capturing portion 22 are integrally combined with each other. As illustrated in FIG. 1, the guide pipe 18 includes a shank 44, to be described hereinafter, having axial directions, i.e., central axial directions, L. Of the axial directions L, a direction from the grip portion 17 toward an elbow portion 45, to be described hereinafter, is represented by L1, whereas a direction from the elbow portion 45 toward the grip portion 17 by L2.

The endoscope 15 is constructed as a scanning-type endoscope. The endoscope 15, i.e., the main endoscope body 21, is flexible. Therefore, the main endoscope body 21 as it extends through the guide pipe 18 can be bent along the shape of the guide pipe 18. The main endoscope body 21 has its orientation adjustable by the guide pipe 18. As illustrated in FIG. 2, the main endoscope body 21 has a central axis, i.e., optical axis, C defined along its longitudinal directions. A distal-end structure portion, i.e., photodetector, 27 has an optical axis C extending in a direction transverse to the shank 44 of the guide pipe 18. As illustrated in FIG. 1, the main endoscope body 21 can move along the central axis C so as to protrude from a protrusive portion 46 of the guide pipe 18 or so as to be withdrawn back into the protrusive portion 46. The main endoscope body 21 is able to acquire an image on and around the optical axis C.

As illustrated in FIG. 2, the main endoscope body 21 has the distal-end structure portion, i.e., photodetector, 27 that is positioned on a distal-end side along the central axis C, a flexible tube 28 disposed on a proximal-end side along the central axis C compared with the distal-end structure portion 27, a pair of left and right wires, i.e., pull wires, extending in and between a distal-end portion of a sheath 32 and the grip portion 17, a tubular sheath 32 covering the distal-end structure portion 27, the flexible tube 28, and the wires, an illumination window 33, a rotary unit 34, an illumination fiber 35, and a plurality of light-receiving fibers 36. According to the present embodiment, the sheath 32 is of a structure capable of being bent horizontally or vertically in unison with the main endoscope body 21, i.e., the flexible tube 28, as illustrated in FIG. 1.

As illustrated in FIG. 1, the grip portion 17 also includes an advancing and retracting mechanism 25 for advancing and retracting the main endoscope body 21 along the axial directions L with respect to the guide pipe 18. The advancing and retracting mechanism 25 includes a knob for advancing and retracting a support unit 26. The main endoscope body 21 is guided by the guide pipe 18 when it is advanced and retracted by the advancing and retracting mechanism 25. During a medical examination on a medical examinee, the user inserts the guide pipe 18 into a cavity, i.e., a nasal cavity 55 (see FIG. 5), a paranasal cavity, or the like, of the medical examinee, and uses the advancing and retracting mechanism 25, etc. to protrude the distal-end structure portion, i.e., photodetector, 27 of the main endoscope body 21 from the protrusive portion 46 or withdraw the distal-end structure portion 27 back into the protrusive portion 46, or uses the bend actuator 23 to change the bent angle of the main endoscope body 21. The user can obtain desired images in the cavity through these movements.

The bend actuator 23 has the support unit 26 slidably housed in the grip portion 17 for sliding movement in the axial directions L of the guide pipe 18, a shaft 37 rotatably supported on the support unit 26, a dial, i.e., knob or rotary knob 38 fixed to an end of the shaft 37, and a sprocket, not illustrated, fixedly mounted on the other end of the shaft 37 within a casing of the support unit 26. The shaft 37 projects out of the grip portion 17 through an oblong hole 41 defined in the grip portion 17. The wires referred to hereinbefore have ends connected to a chain held in mesh with the sprocket. As the dial 38 rotates, one of the wires is pulled and the other wire is slackened, pulling the distal end of the sheath 32 to bend the sheath 32 to the left or right in FIG. 1. When the sheath 32 is thus bent, the main endoscope body 21, i.e., the flexible tube 28 disposed therein is bent. The directions in which the sheath 32 is bent are by way of example only. The sheath 32 may be bent toward or away from the viewer of FIG. 1, or may be curved in four directions, i.e., upward, downward, leftward, and rightward directions, with four wires used. The wires, i.e., filamentary members, as they are pulled can adjust the bent angle of the endoscope 15, i.e., the main endoscope body 21.

As illustrated in FIG. 2, the illumination fiber 35 is optically connected to a light source disposed adjacent to the controller 13. The light-receiving fibers 36 are optically connected to a light detector 42. The light-receiving fibers 36 have distal ends exposed outwardly near the distal-end structure portion 27. Therefore, the endoscope 15 is able to acquire images from the distal-end structure portion 27 through the light-receiving fibers 36. Specifically, the endoscope 15 is able to acquire images around the optical axis C illustrated in FIG. 2 through the light-receiving fibers 36.

As illustrated in FIG. 2, the endoscope image capturing portion 22 includes the light detector 42 that is of general nature. The endoscope image capturing portion 22 is capable of acquiring images obtained from the distal-end structure portion 27 of the main endoscope body 21. Specifically, the light detector 42 converts light from the light-receiving fibers 36 into an electric signal and sends the electric signal to the controller 13.

The rotary unit 34 is electrically connected to the controller 13. The rotary unit 34 is in the form of an electric motor or the like, and swings in a swirling pattern, for example, under the control of the controller 13, i.e., a motor driver 43 thereof. The illumination fiber 35 has a distal end 35A that swings in a swirling pattern in response to the movement of the rotary unit 34. Therefore, a subject to be imaged has a surface scanned in a swirling pattern by illuminating light applied from the illumination fiber 35 through the distal end 35A thereof and the illumination window 33. The light-receiving fibers 36 receive returning light from the subject and guide the received light to the light detector 42. The light detector 42 converts the received light from the light-receiving fibers 36 into an electric signal and sends the electric signal to the controller 13. The controller 13 converts the electric signal into an image, appropriately processes the image, and displays the image on the display device 14.

Figure 4:
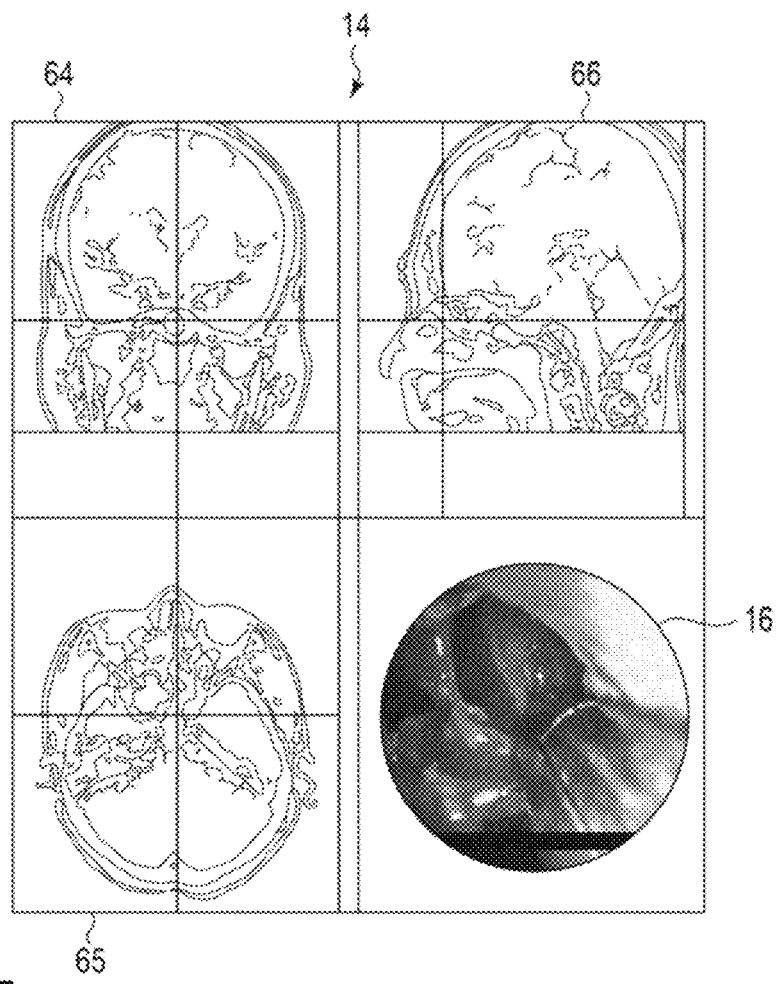
FIG. 4 is a schematic diagram illustrating an image and sectional images displayed on a display device illustrated in FIG. 1.

FIG. 4 illustrates images displayed on the display device 14. The display device 14 displays the coronal section image 64 obtained by the sectional image acquiring device 5, the axial section image 65 obtained by the sectional image acquiring device 5, the sagittal section image 66 obtained by the sectional image acquiring device 5, and the image 16 obtained by the main endoscope body 21. Therefore, the user can confirm the four images 64 through 66 and 16 on one screen displayed on the display device 14.

Figure 3:
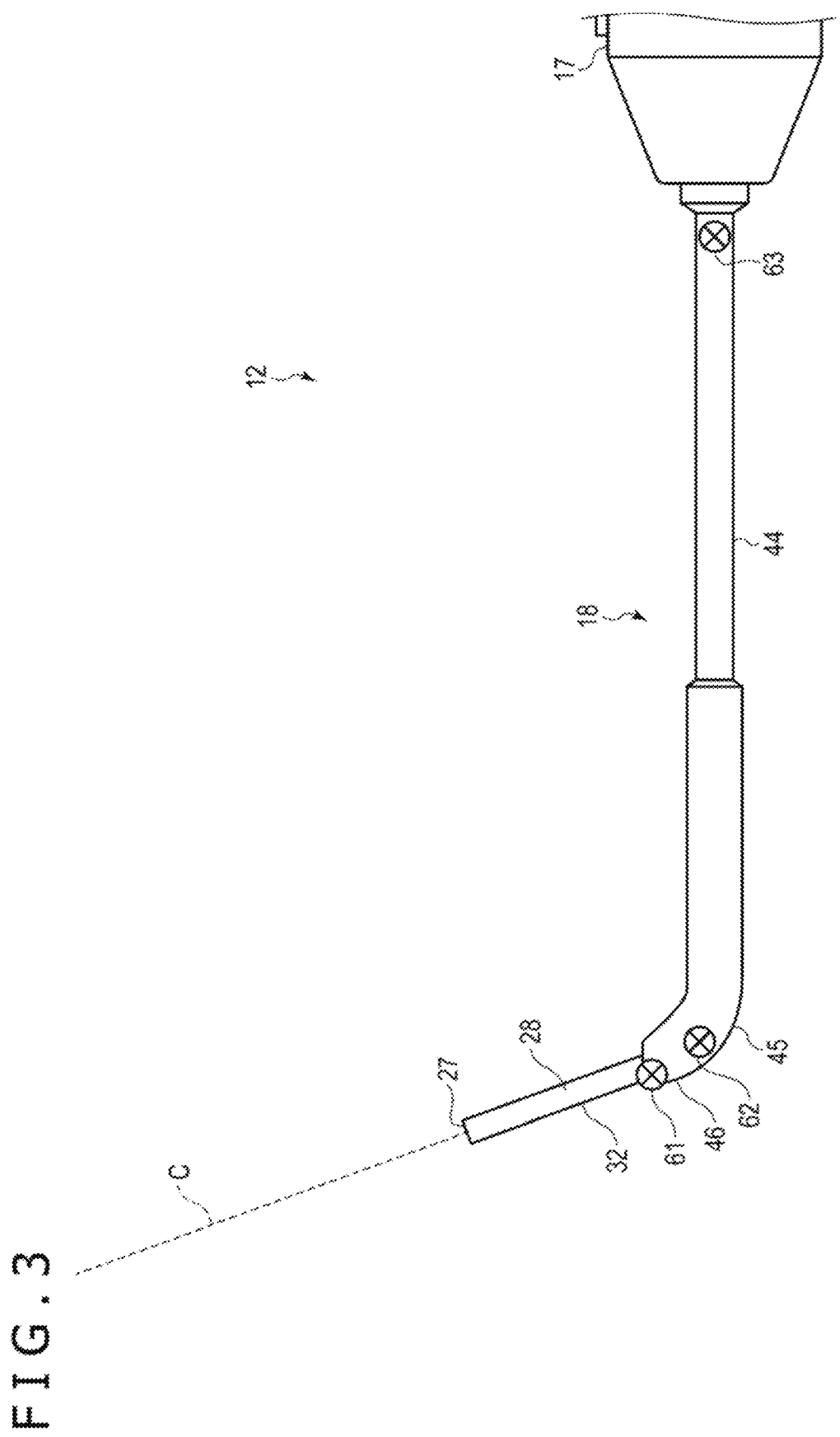
FIG. 3 is a side elevational view illustrating a guide pipe and a main endoscope body of the endoscopic system illustrated in FIG. 1.

As illustrated in FIGS. 1 and 3, the guide pipe, i.e., a guide portion, 18 is substantially L-shaped in its entirety, and is of a tubular shape, i.e., a hollow cylindrical shape, bent into an elbow configuration. The guide pipe 18 includes the shank 44 that has an end attached to the grip portion 17, the elbow portion 45 attached to the other end of the shank 44, and the protrusive portion 46 protruding in a direction, i.e., a lateral direction, transverse to the direction in which the shank 44 extends from the elbow portion 45. The guide pipe 18 includes the first probe 61 that is disposed near the distal end of the protrusive portion 46, the second probe 62 that is disposed on the elbow portion 45, i.e., the shank 44, and the third probe 63 that is disposed on a base of the shank 44. Each of the first probe 61, the second probe 62, and the third probe 63 is in the form of a small piece of metal, for example. The position of each of the first probe 61, the second probe 62, and the third probe 63 in a three-dimensional space is detected by the navigation system 8 that is constructed as the magnetic sensor.

The first probe 61 is disposed on or around the optical axis C at a position off the shank 44. The second probe 62 is disposed at a position where the shank 44 and the optical axis C intersect with each other. The third probe 63 is disposed on the shank 44 at a position off the position where the second probe 62 is disposed.

In a case where the navigation system 8 includes an optical sensor, the first probe 61, the second probe 62, and the third probe 63 are constructed respectively as infrared radiation reflecting spheres, for example. The navigation system 8 detects the positions of the first probe 61, the second probe 62, and the third probe 63 in a three-dimensional space.

The first probe 61, the second probe 62, and the third probe 63 should preferably be identifiable from each other by the navigation system 8.

The main endoscope body 21 can be inserted through the guide pipe 18. The guide pipe 18 has an inner wall that can guide the main endoscope body 21 for advanced and retracted movement along the central axis C. Although the guide pipe 18 should preferably be fixed to the grip portion 17, for example, it may be rotatable about the axial directions L with respect to the grip portion 17. In such a case, the grip portion 17 may have a rotary knob for rotating the guide pipe 18 about the axial directions L.

The controller 13 illustrated in FIG. 1 has a main controller body 47 in the form of a general computer and a power supply 48 separate from the main controller body 47. The main controller body 47 includes a housing 51, a circuit board 52 housed in the housing 51, a CPU (Central Processing Unit), a ROM (Read-Only Memory), and a RAM (Random Access Memory) that are mounted on the circuit board 52, and an HDD (Hard Disk Drive) 53. The main controller body 47 also includes first software installed in the HDD 53 for controlling the insertion device 12 in various ways, second software installed in the HDD 53 for processing, i.e., rotating, making color tone corrections on, etc. the image 16 and the images 64 through 66 and displaying them to the display device 14, third software installed in the HDD 53 for acquiring the positions of the first through third probes 61 through 63 via the navigation system 8, and a motor driver 43 housed in the housing 51 for controlling the rotary unit 34.

Prior to diagnoses and observations, the controller 13 can store a first reference direction and a second reference direction that are preset by the user, as vector quantities or the like. The second software makes it possible to display the coronal section image 64 about the position of the first probe 61, the axial section image 65 about the position of the first probe 61, the sagittal section image 66 about the position of the first probe 61, and the image 16 obtained from the endoscope 15, i.e., an endoscope image, in an array on the display device 14.

The power supply 48 can supply electric power to the rotary unit 34. The main controller body 47 can control various components of the insertion device 12 as follows, for example. The main controller body 47 can control the rotary unit 34 through the motor driver 43 to adjust its rotational speed, etc. The main controller body 47 can control the light source to adjust the amount of light supplied therefrom to the illumination fiber 35. The main controller body 47 can process an electric signal representing an image acquired by the light detector 42 of the insertion device 12 to convert the electric signal into an image 16 and display the image 16, i.e., an endoscope image, on the display device 14.

An observational method using the image diagnosing system 1 and the endoscopic system 11 according to the present embodiment will be described hereinafter with reference to FIGS. 5 through 11.

Of the paranasal cavity of a human body, a maxillary sinus is positioned essentially centrally in the face as branches extending laterally from the nasal cavity 55 that extends in the anterior posterior directions. Between the nasal cavity and the maxillary sinus, there exists a middle nasal concha, etc. that is an organ dividing the nasal cavity and the maxillary sinus from each other. For observing the maxillary sinus with the endoscopic system, it is necessary to insert the main endoscope body 21 into the nasal cavity 55 to a middle position in the anterior posterior directions of the medical examinee and then direct the distal-end structure portion 27 of the main endoscope body 21 and the optical axis C to an angle of approximately 110° laterally from the posterior direction of the medical examinee.

Figure 5:
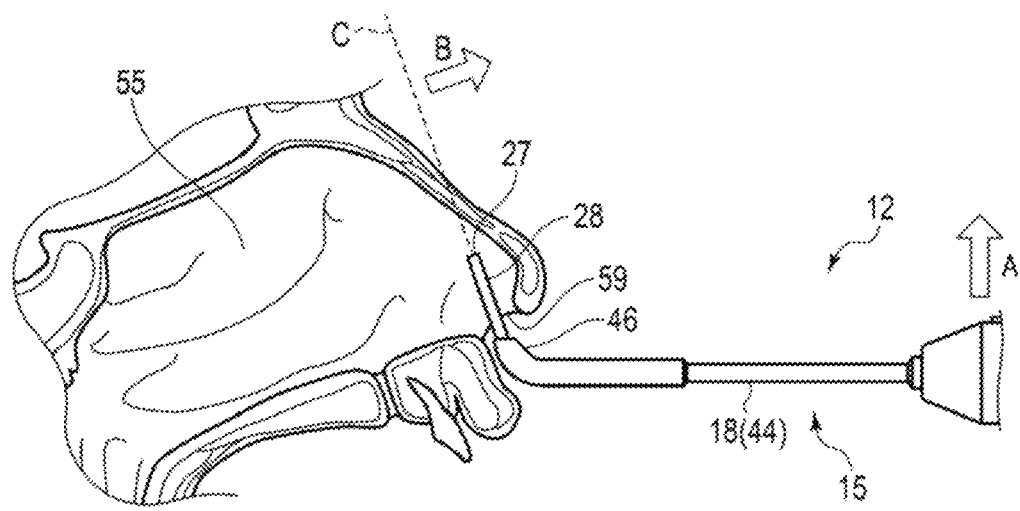
FIG. 5 is a side elevational view schematically illustrating the manner in which a portion of an insertion device is inserted into a hole, i.e., a nasal cavity, of the medical examinee.
Figure 6:
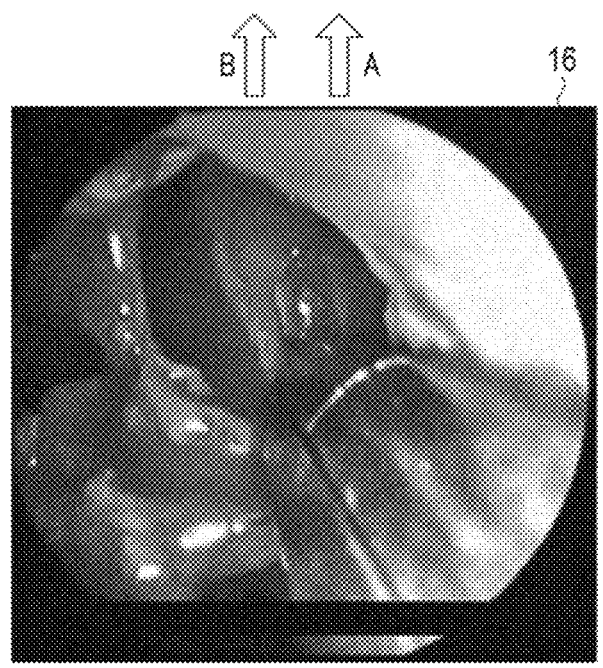
FIG. 6 is a schematic diagram illustrating an image, i.e., an endoscope image, obtained from the main endoscope body of the insertion device illustrated in FIG. 5.

In the examination, the doctor who is the user can insert the main endoscope body 21 from a nostril 59 into the nasal cavity 55 of the medical examinee, for example, as illustrated in FIG. 5. In FIG. 5, the guide pipe 18 is illustrated as being inserted into the right fossa of the nasal cavity 55 of the medical examinee. At this time, the protrusive portion 46 of the guide pipe 18 protrudes in the superior direction of the medical examinee. As illustrated in FIG. 5, when the user lifts the grip portion 17 by hand in the superior direction, indicated by the arrow A, of the medical examinee, the image 16 obtained from the main endoscope body 21 also moves substantially upwardly as indicated by the arrow B. The image 16 as it moves in this way is illustrated in FIG. 6. In FIG. 6, the direction in which the user lifts the grip portion 17 as indicated by the arrow A and the direction in which the image 16 scrolls as indicated by the arrow B are the same as each other. When the endoscope 15 is in such a positional relationship, the user is not confused.

Figure 7:
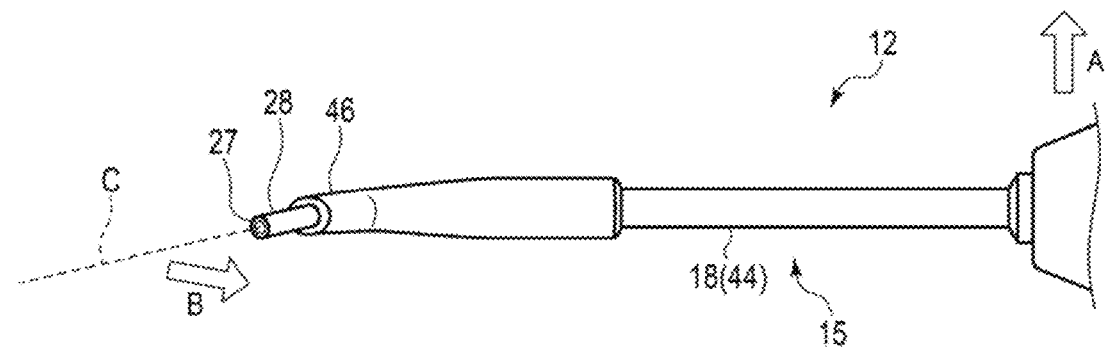
FIG. 7 is a side elevational view schematically illustrating the manner in which a grip portion has been turned counterclockwise through approximately 90° from the state illustrated in FIG. 5.
Figure 8:
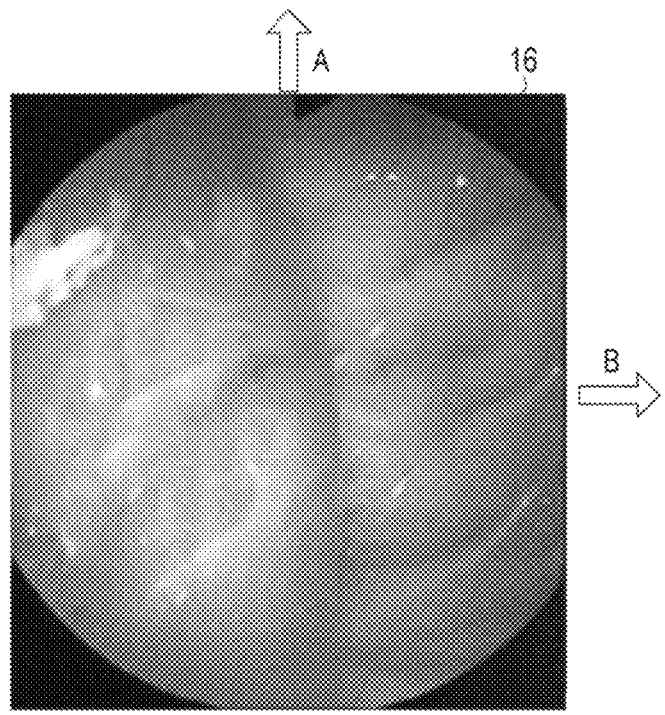
FIG. 8 is a schematic view is a schematic diagram illustrating an image, i.e., an endoscope image, obtained from the main endoscope body of the insertion device illustrated in FIG. 7.

On the other hand, when the user turns the grip portion 17 counterclockwise through approximately 90°, for example, the protrusive portion 46 protrudes in a lateral direction of the medical examinee, as illustrated in FIG. 7. In this case, as illustrated in FIG. 8, the vertical positional relationship of the image 16 obtained from the main endoscope body 21 is turned approximately 90° from the vertical positional relationship of the image 16 illustrated in FIG. 6. In FIG. 8, the rightward direction corresponds to the superior direction of the medical examinee. When the user then lifts the grip portion 17 in the superior direction of the medical examinee as indicated by the arrow A, the image 16 scrolls in the rightward direction indicated by the arrow B, as illustrated in FIG. 8. These movements are indicated by the arrows A and B in FIG. 7. In a case where the direction in which the user moves its hand and the direction in which the image 16 scrolls are thus different from each other, the user tends to fail to know which direction in the actual space corresponds to the direction in the image 16 that the user is seeing at present.

In order to improve such a situation, according to the present embodiment, the controller 13 performs a process of establishing a second reference direction 72 (see FIGS. 9 and 10) in the image 16, i.e., the endoscope image, obtained from the main endoscope body 21 with respect to a first reference direction 71 (see FIG. 10) determined in the actual space by the user, and bringing the second reference direction 72 into agreement with the first reference direction 71. For example, when the endoscope 15 is the positional relationship illustrated in FIG. 5, that is, when the direction in which the protrusive portion 46 protrudes, i.e., the direction from the second probe 62 toward the first probe 61, is the same as the superior direction of the medical examinee, the user carries out a calibration step for establishing the first reference direction 71 and the second reference direction 72.

Figure 9:
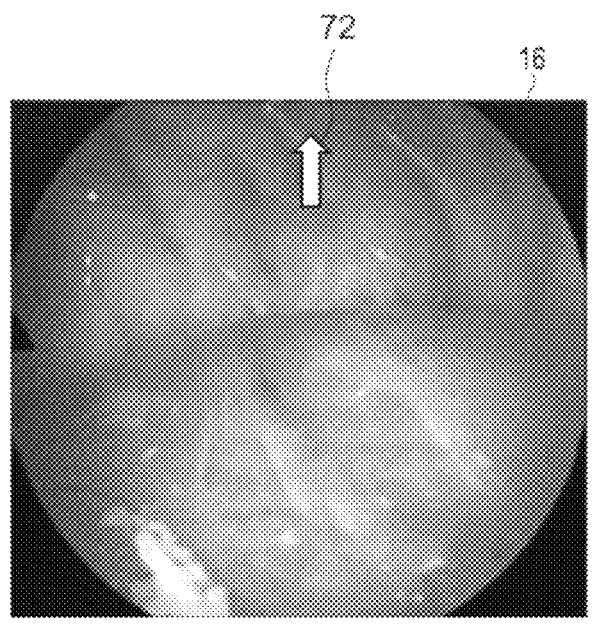
FIG. 9 is a schematic diagram illustrating an arrow indicating a second reference direction in the image displayed on the display device in a calibration step.
Figure 10:
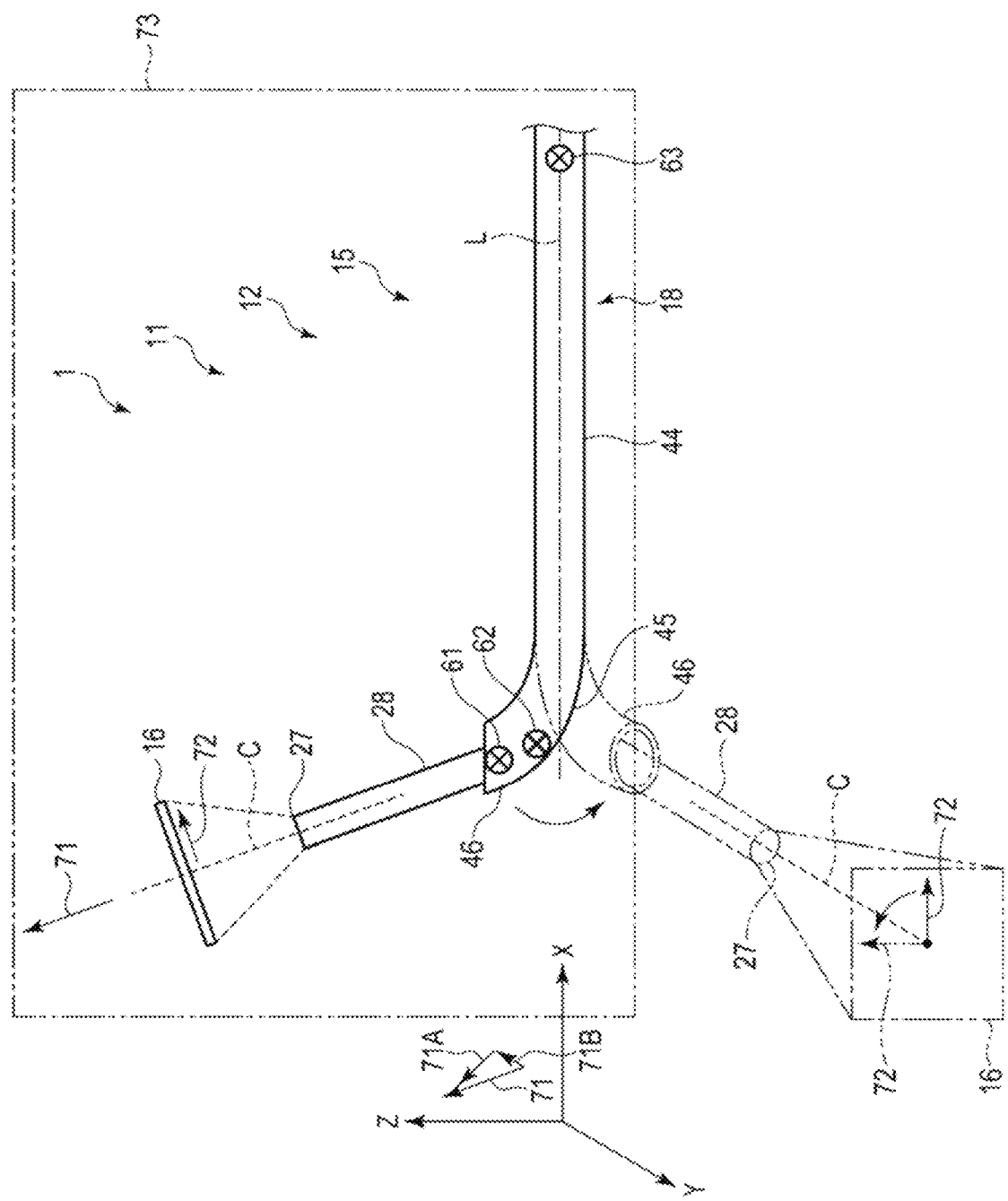
FIG. 10 is a schematic view schematically illustrating the relationship between a first reference direction and the second reference direction and the concept of bringing the second reference direction into agreement with the first reference direction.
Figure 11:
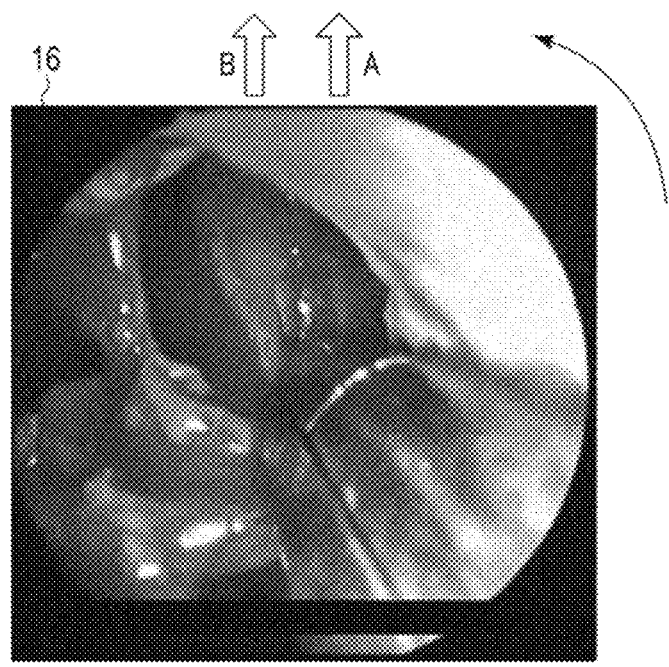
FIG. 11 is a schematic diagram illustrating the manner in which the image has been turned counterclockwise through 90° to bring the second reference direction in the image into substantial agreement with the first reference direction in actual space.

In the calibration step, the first reference direction 71 and the second reference direction 72 can be determined arbitrarily by the user on a calibration screen illustrated in FIG. 9. The user uses a switch 54 or the like on the controller 13 to determine various items or variables. As illustrated in FIG. 10, the controller 13 may establish the direction from the second probe 62 toward the first probe 61 as the first reference direction 71 in the actual space at a predetermined timing, for example. For example, in a case where the user establishes the first reference direction 71 at the timing when the insertion device 12 is in the positional relationship illustrated in FIG. 5, the first reference direction 71 becomes the direction from the second probe 62 toward the first probe 61, which is the superior direction recognized in the actual space by the user. The first reference direction 71 may be established in an arbitrary way. For example, the direction from the first probe 61 toward the second probe 62 may be established as the first reference direction 71 in the actual space. In a case where the user establishes the first reference direction 71 in this way when the insertion device 12 is in the positional relationship illustrated in FIG. 5, the first reference direction 71 becomes the jaw direction, i.e., inferior direction, recognized in the actual space by the user.

As illustrated in FIGS. 9 and 10, in the calibration step, the user can establish the second reference direction 72 corresponding to the first reference direction 71 in the image 16, i.e., the endoscope image. In the calibration step, a step of establishing the second reference direction 72 should preferably be carried out at the same time that the first reference direction 71 is established.

The user can establish the second reference direction 72 by selecting either one of two directions parallel to a plane 73 that passes through the first probe 61, the second probe 62, and the third probe 63 in the image 16. In this case, as illustrated in FIG. 9, the user can establish an upward direction in FIG. 16 as the second reference direction 72, for example. The arrow that indicates the second reference direction 72 in the image 16 may displayed in the image 16 or may be erased from display in the image 16 after a predetermined time has elapsed. In a case where the jaw direction of the medical examinee is established as the first reference direction 71, a downward direction in the image 16, for example, may be established as the second reference direction 72.

At this time, the controller 13 grasps the posture of the insertion device 12 at the time the first reference direction 71 and the second reference direction 72 are established in the calibration step, from the positions, i.e., coordinates, in the actual space of the first probe 61, the second probe 62, and the third probe 63.

In a case where the user turns the grip portion 17 counterclockwise approximately 50° to 140° around the axial directions L from the position indicated by the solid lines in FIG. 10 to the position indicated by the two-dot-and-dash lines in FIG. 10, the second reference direction 72 in the image 16 deviates from the first reference direction 71, e.g., the superior direction, in the actual space. According to the present embodiment, the controller 13 grasps the angle through which the direction from the second probe 62 toward the first probe 61 or the direction from the first probe 61 toward the second probe 62 has turned from the first reference direction 71. When the angle exceeds a threshold value, the controller 13 performs an image processing process for turning the image 16 clockwise through 90°, for example. In this manner, the controller 13 can bring the second reference direction 72 in the image 16 into substantial agreement with the first reference direction 71 in the actual space. The angle through which to turn the image 16 clockwise may not be 90°.

The controller 13 is able to define an X-axis, a Y-axis, and a Z-axis. The X-axis is defined along a direction parallel to the axial directions L of the shank 44. An X-Y plane corresponds to a horizontal plane, for example, and the Z-axis to vertical directions, for example. The controller 13 may turn the image 16 such that when the vector of the first reference direction 71 is resolved into a first component 71A parallel to an X-Z plane and another second component 71B, i.e., a Y-direction component, the vector of the first component 71A parallel to the X-Z plane becomes parallel to the second reference direction 72. In this manner, the controller 13 can bring the second reference direction 72 in the image 16 into more accurate agreement with the first reference direction 71 in the actual space.

According to the present embodiment, the threshold value can be set to 45°, for example. However, the threshold value may be set to an arbitrary magnitude such as 30°, 60°, or the like.

On the other hand, in a case where the user turns the grip portion 17 clockwise, the controller 13 grasps the angle through which the direction from the second probe 62 toward the first probe 61 or the direction from the first probe 61 toward the second probe 62 has turned from the first reference direction 71. When the angle exceeds a threshold value of 45°, 30°, 60°, or the like, for example, the controller 13 performs an image processing process for turning the image 16 counterclockwise through approximately 90°, for example. In this manner, the controller 13 can bring the second reference direction 72 in the image 16 into substantial agreement with the first reference direction 71 in the actual space. The controller 13 may turn the image 16 such that when the vector of the first reference direction 71 is resolved into the first component 71A parallel to the X-Z plane and the other second component 71B, i.e., the Y-direction component, the vector of the first component 71A parallel to the X-Z plane becomes parallel to the second reference direction 72. In this manner, the controller 13 can bring the second reference direction 72 in the image 16 into more accurate agreement with the first reference direction 71 in the actual space.

The process described hereinbefore in which the controller 13 brings the second reference direction 72 in the image 16 into agreement with the first reference direction 71 in the actual space as described hereinbefore is an example of process for indicating the first reference direction 71 to the user. Since the treatment for bringing the second reference direction 72 in the image 16 into agreement with the first reference direction 71 in the actual space is carried out, the user is able to diagnose and observe the nasal cavity 55 and the paranasal cavity, i.e., maxillary sinus, smoothly without losing directions in the image 16.

According to the first embodiment, the following features are covered. The endoscopic system 11 includes the endoscope 15 having the shank 44 and the photodetector having the optical axis C in the direction transverse to the shank 44, the display device 14 for displaying the image 16 acquired through the photodetector, the first probe 61 disposed in the endoscope 15 on or around the optical axis C at the position off the shank 44, the second probe 62 disposed in the endoscope 15 at or near the position where the shank 44 and the optical axis C intersect with each other, the sensor for detecting the position of the first probe 61 and the position of the second probe 62, and the controller 13 for acquiring the direction from the second probe 62 toward the first probe 61 or the direction from the first probe 61 toward the second probe 62 as a direction of the optical axis C.

With this arrangement, the controller 13 is capable of acquiring the direction of the optical axis C. The direction of the optical axis C of the photodetector grasped by the controller 13 can be used in various applications, e.g., for grasping the direction of the optical axis C that is preferred by the user, for determining whether the endoscope is used with the optical axis C or without the optical axis C, for indicating the grasped direction of the optical axis C to the user, etc.

After having established the direction from the second probe 62 toward the first probe 61 or the direction from the first probe 61 toward the second probe 62 as the first reference direction 71 in the actual space, the controller 13 performs a process of indicating the first reference direction 71 to the user in the image 16 displayed on the display device 14 when the angle formed between the direction from the second probe 62 toward the first probe 61 or the direction from the first probe 61 toward the second probe 62 and the first reference direction 71 exceeds the predetermined threshold value.

With this arrangement, as the process for indicating the direction to the user in the image 16 displayed on the display device 14 is carried out, the user or the like is prevented from failing to know which direction in the actual space corresponds to the direction that the user or the like sees in the image 16. The endoscopic system 11 is thus rendered user-friendly.

The controller 13 establishes the second reference direction 72 corresponding to the first reference direction 71 in the image 16. The process for indicating the first reference direction 71 to the user is a process for turning the image 16 to bring the second reference direction 72 into agreement with the first reference direction 71. With this arrangement, the image 16 displayed on the display device 14 can easily be understood most intuitively by the user. The endoscopic system 11 is thus rendered user-friendly.

The endoscopic system 11 includes the third probe 63 disposed on the shank 44 at the position off the position where the second probe 62 is disposed, and whose position can be detected by the navigation system 8. With this arrangement, the first probe 61, the second probe 62, and the third probe 63 allow the controller 13 to grasp a plane in which the endoscope 15 is placed. Furthermore, the controller 13 is also able to grasp the posture of the endoscope 15.

The second reference direction 72 is established on a plane defined by the first probe 61, the second probe 62, and the third probe 63.

With this arrangement, the second reference direction 72 can be established highly simply in the image 16 obtained from the endoscope 15. The endoscopic system 11 is thus rendered user-friendly as the user is prevented from feeling puzzled about how to operate the endoscopic system 11 while using the endoscopic system 11.

The endoscope 15 has the tubular guide portion including the shank 44 and the protrusive portion 46 that protrudes from the shank 44 in the direction transverse to the direction in which the shank 44 extends, and the main endoscope body 21 having the photodetector and movable in the guide portion for advanced and retracted movement to project the photodetector from the protrusive portion 46, the main endoscope body 21 being guided by the guide portion when advanced and retracted.

With this arrangement, even though the endoscope 15 is of the configuration in which it is guided by the guide portion, the endoscopic system 11 is user-friendly as it is easy for the user to recognize which direction in the actual space corresponds to the direction in the image 16 that the user is seeing.

The first probe 61 is disposed on the protrusive portion 46, and the second probe 62 is disposed on the shank 44. With this arrangement, the first probe 61 and the second probe 62 can be disposed on the guide portion. The main endoscope body 21 can thus be reduced in size. Therefore, the main endoscope body 21 has better access to narrow spaces in the body of the medical examinee.

The image diagnosing system includes the endoscopic system 11 and the sectional image acquiring device 5 for acquiring at least one sectional image of the medical examinee. The controller 13 displays the image 16 and the at least one sectional image in an array on the display device 14. With this arrangement, the user can make diagnoses and observations while simultaneously confirming both the image 16 obtained from the endoscope 15 and the sectional image obtained from the sectional image acquiring device 5.

Modification of the First Embodiment

Figure 12:
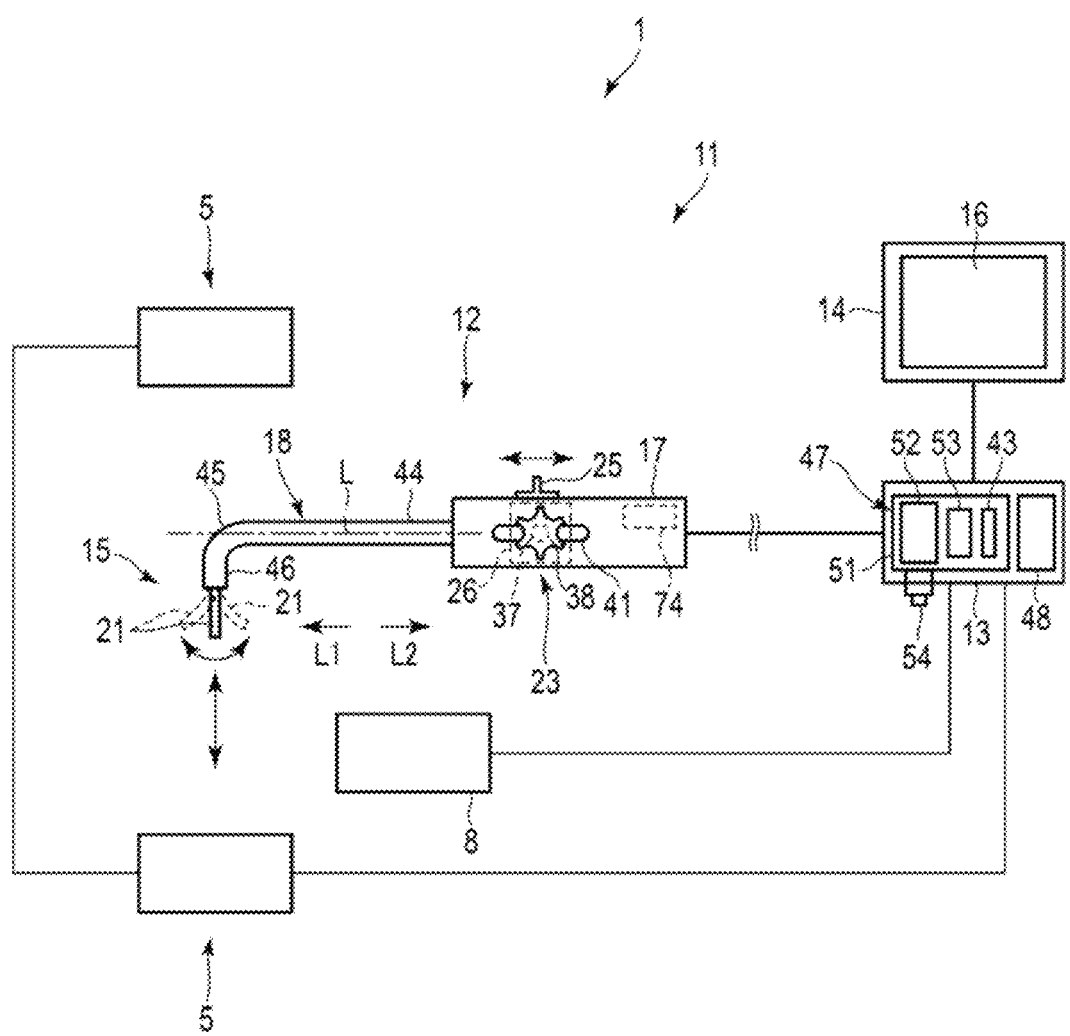
FIG. 12 is a schematic view illustrating the overall makeup of an image diagnosing system and an endoscopic system according to a modification of the first embodiment.

A modification of the first embodiment will be described hereinafter with reference to FIG. 12. Hereinafter, those portions of the modification which are different from the first embodiment will chiefly be described, and the description of those portions which are the same as those of the first embodiment will be omitted. According to the present modification, the calibration step required in the first embodiment is dispensed with.

According to the present modification, the endoscopic system 11 has a gravitational direction detector 74. The gravitational direction detector 74 should preferably be disposed in the protrusive portion 46 of the guide pipe 18, though it may be disposed in the grip portion 17. The gravitational direction detector 74 may be in the form of a gravity sensor, for example. The gravitational direction detector 74 is able to detect the gradient of the direction in which the protrusive portion 46 extends with respect to the vertical directions. The gravitational direction detector 74 represents an example of second sensor.

The controller 13 acquires information from the gravitational direction detector 74 at any time, and stores a vertically upward direction as the first reference direction 71. The controller 13 may alternatively store a vertically downward direction as the first reference direction 71 based on the information from the gravitational direction detector 74. The controller 13 acquires and stores information regarding the direction in which the protrusive portion 46 extends at present, i.e., the posture thereof, through the gravitational direction detector 74. The second reference direction 72 is established in the same manner as with the first embodiment.

The controller 13 and the second software stored in the controller 13 perform a process for turning the image 16 obtained in the endoscopic system 11 in a predetermined direction when the direction in which the protrusive portion 46 extends exceeds a predetermined threshold value with respect to the first reference direction 71, based on the information from the gravitational direction detector 74. According to the present modification, therefore, the calibration step according to the first embodiment is not necessary during an observational method using the image diagnosing system 1 and the endoscopic system 11.

An observational method using the image diagnosing system 1 and the endoscopic system 11 according to the present modification will be described hereinafter.

In an examination, the doctor who is the user inserts the main endoscope body 21 from a nostril 59 into the nasal cavity, i.e., hole 55, of the medical examinee at the posture illustrated in FIG. 5, for example.

When the user turns the grip portion 17 counterclockwise through approximately 50° to 140° from the state illustrated in FIG. 5 to the state illustrated in FIG. 7, the protrusive portion 46 protrudes in a lateral direction of the medical examinee. In this case, the vertical positional relationship of the image 16 obtained from the main endoscope body 21 and the endoscope image capturing portion 22 turns counterclockwise through approximately 90° from the vertical positional relationship of the image 16 before it is turned.

According to the present modification, the controller 13 grasps the angle through which the direction in which the protrusive portion 46 extends has turned from the first reference direction 71 based on the information from the gravitational direction detector 74. When the angle exceeds a threshold value, the controller 13 performs an image processing process for turning the image 16 clockwise through 90°, for example. The controller 13 can thus bring the second reference direction 72 in the image 16 into agreement with the first reference direction 71, i.e., the vertically upward direction.

According to the present modification, the threshold value can be set to 45°, for example. However, the threshold value may be set to an arbitrary magnitude such as 30°, 60°, or the like.

On the other hand, when the user turns the grip portion 17 clockwise from the state illustrated in FIG. 5, the controller 13 grasps the angle through which the direction in which the protrusive portion 46 extends has turned from the first reference direction 71 based on the information from the gravitational direction detector 74. When the angle exceeds a threshold value of 45°, 30°, 60°, or the like, for example, the controller 13 performs an image processing process for turning the image 16 counterclockwise through approximately 90°, for example. In this manner, the controller 13 brings the second reference direction 72 in the image 16 into substantial agreement with the first reference direction 71, i.e., the vertically upward direction.

In this observational method, the vertically downward direction may be established as the first reference direction 71, and the downward direction of the image 16 as the second reference direction 72. In this case, too, the angle of the direction in which the protrusive portion 46 protrudes from the vertically downward direction is calculated, and when the angle from the vertically downward direction becomes smaller than a threshold value of 135°, 150°, 120°, or the like, the image 16 is turned counterclockwise or clockwise through approximately 90°, for example, bringing the second reference direction 72 in the image 16 into agreement with the first reference direction 71, i.e., the vertically downward direction.

According to the present modification, the endoscope 15 has the second sensor capable of detecting vertical directions, and the first reference direction 71 is either the vertically upward direction or the vertically downward direction. With this arrangement, since the second sensor can detect the vertical directions accurately, in a case where the user rotates the endoscope 15 to cause the vertical directions in the image 16 to deviate from the vertical directions in the actual space, the vertical directions in the image 16 can be brought into accurate agreement with the vertical directions in the actual space.

Second Embodiment

An endoscopic system 11 according to a second embodiment and an image diagnosing system 1 using the endoscopic system 11 according to the second embodiment will be described hereinafter with reference to FIGS. 13 and 14. According to the second embodiment, the process of indicating directions to the user is different from the first embodiment, whereas other portions of the second embodiment are the same as those of the first embodiment. Hereinafter, those portions of the second embodiment which are different from the first embodiment will chiefly be described, and the illustration or description of those portions which are the same as those of the first embodiment will be omitted.

According to the present embodiment, the second software installed in the HDD 53 not only processes, i.e., makes color tone corrections on, etc. the image 16 and the sectional images, but also displays two arrows for indicating the second reference direction 72 in the image 16 obtained from the endoscope 15. The two arrows include a superior arrow 72A representing the superior direction of the medical examinee in the image 16 and a jaw arrow 72B representing a jaw direction of the medical examinee in the image 16. The superior arrow 72A and the jaw arrow 72B are identifiable from each other. For example, the letters "superior side" may be added in the vicinity of, for example, the superior arrow 72A, and the letters "jaw side" may be added in the vicinity of, for example, of the jaw arrow 72B. The superior arrow 72A and the jaw arrow 72B may be made identifiable from each other by this approach.

An observational method using the image diagnosing system 1 and the endoscopic system 11 according to the present embodiment will be described hereinafter with reference to FIGS. 13 and 14.

In the examination, the doctor who is the user can insert the main endoscope body 21 from a nostril 59 into the nasal cavity 55 of the medical examinee, for example. For example, when the endoscope 15 is the positional relationship illustrated in FIG. 5, that is, when the endoscope 15 is the positional relationship in which the direction from the second probe 62 toward the first probe 61 is the superior direction of the medical examinee, the user can perform the calibration step that is a step for establishing the first reference direction 71 and the second reference direction 72. In the calibration step, the first reference direction 71 is established in the same manner as with the first embodiment. In the calibration step, a step of establishing the second reference direction 72 should preferably be carried out at the same time that the first reference direction 71 is established.

In the calibration step, the user can establish the second reference direction 72 corresponding to the first reference direction 71 in the image 16. As illustrated in FIG. 13, in the calibration step, the user can establish the superior direction of the medical examinee as a superior arrow 72A representing the second reference direction 72 and establish the jaw direction of the medical examinee as a jaw arrow 72B representing the second reference direction 72. Specifically, the controller 13 prompts, in a calibration screen, the user to select either one of two directions parallel to a plane that passes through the first probe 61, the second probe 62, and the third probe 63 in the image 16, as an upward direction in the image 16, i.e., the superior arrow 72A representing the second reference direction 72, and to select the other as a downward direction in the image 16, i.e., the jaw arrow 72B representing the second reference direction 72. By thus prompting the user to select the directions, the controller 13 can establish the superior arrow 72A representing the second reference direction 72 and the jaw arrow 72B representing the second reference direction 72. The superior arrow 72A and the jaw arrow 72B representing the second reference direction 72 thus established are displayed as they are in the image 16.

At this time, the direction from the second probe 62 toward the first probe 61 corresponds to the superior arrow 72A representing the second reference direction 72. The direction from the first probe 61 toward the second probe 62 corresponds to the jaw arrow 72B representing the second reference direction 72. The controller 13 stores the first reference direction 71 and the second reference direction 72, i.e., the superior arrow 72A and the jaw arrow 72B, as vector quantities or the like. The calibration step may naturally be carried out when the endoscope 15 is in the positional relationship in which the direction from the second probe 62 toward the first probe 61 is the jaw direction of the medical examinee.

Figure 13:
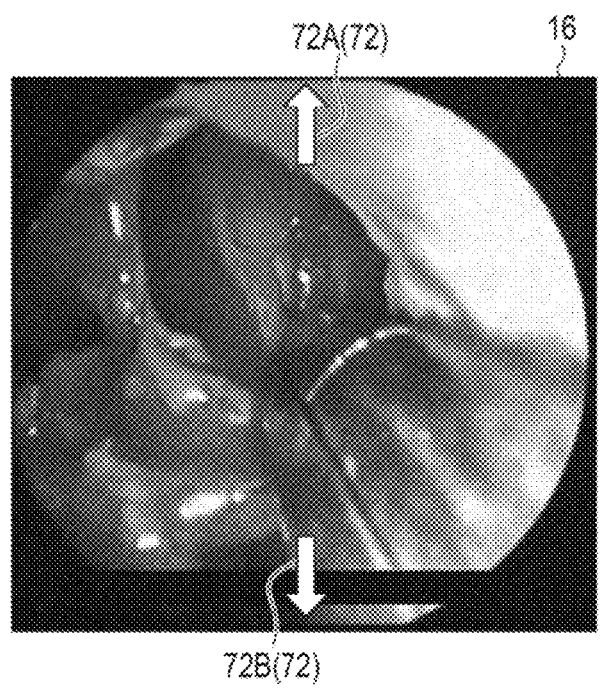
FIG. 13 is a schematic diagram illustrating the second reference direction in the image in an image diagnosing system and an endoscopic system according to a second embodiment.
Figure 14:
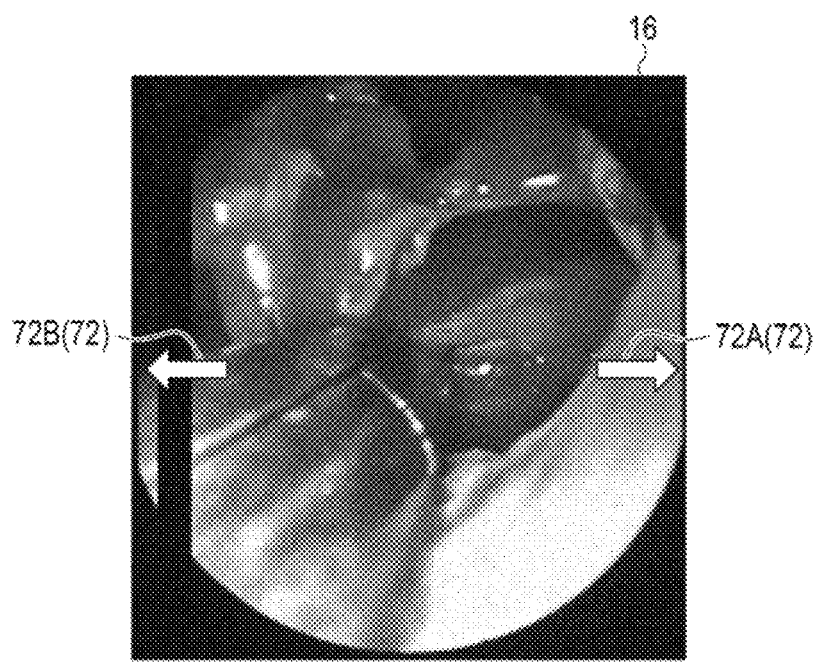
FIG. 14 is a schematic diagram illustrating the manner in which the image and the second reference direction has been turned clockwise through approximately 90° while the grip portion has been turned counterclockwise through approximately 90° from the state illustrated in FIG. 5.

In a case where the user turns the grip portion 17 counterclockwise from the state illustrated in FIG. 5 to the state illustrated in FIG. 7, for example, the vertical positional relationship of the image 16 obtained from the main endoscope body 21 is turned clockwise approximately 90° as illustrated in FIG. 14 from the vertical positional relationship of the image 16 illustrated in FIG. 13. At this time, in FIG. 14, the rightward direction of the image 16 corresponds to the superior direction of the medical examinee, and the leftward direction of the image 16 corresponds to the jaw direction of the medical examinee.

According to the present embodiment, as illustrated in FIG. 14, the superior arrow 72A representing the second reference direction 72 is displayed so as to point to the rightward direction in the image 16 and the jaw arrow 72B representing the second reference direction 72 is displayed so as to point to the leftward direction in the image 16. The user is hereby able to know the superior direction of the medical examinee and the jaw direction of the medical examinee. Therefore, the user is prevented from failing to know directions in the image 16 while diagnosing and observing the medical examinee. The user is thus able to make diagnoses and observations smoothly in the nasal cavity and the paranasal cavity.

On the other hand, in a case where the user turns the grip portion 17 clockwise from the state illustrated in FIG. 5, the vertical positional relationship of the image 16 obtained from the main endoscope body 21 is turned counterclockwise approximately 90° from the vertical positional relationship of the image 16 illustrated in FIG. 13. At this time, the leftward direction of the image 16 corresponds to the superior direction of the medical examinee, and the rightward direction of the image 16 corresponds to the jaw direction of the medical examinee. According to the present embodiment, the superior arrow 72A representing the second reference direction 72 is displayed so as to point to the leftward direction in the image 16 and the jaw arrow 72B representing the second reference direction 72 is displayed so as to point to the rightward direction in the image 16. The user is hereby able to know the superior direction of the medical examinee and the jaw direction of the medical examinee in the image 16. Therefore, the user is prevented from failing to know directions in the image 16 while diagnosing and observing the medical examinee. The user is thus able to make diagnoses and observations smoothly in the nasal cavity and the paranasal cavity.

According to the present embodiment, the controller 13 establishes the second reference direction 72 corresponding to the first reference direction 71 in the image 16. The process for indicating the first reference direction 71 to the user is a process for displaying the second reference direction 72 in the image 16. With this arrangement, since the user is able to know directions in the image 16 obtained from the endoscope 15, the user is prevented from failing to know directions in the image 16 while diagnosing and observing the medical examinee. The endoscopic system 11 is thus rendered user-friendly.

Third Embodiment

Figure 15:
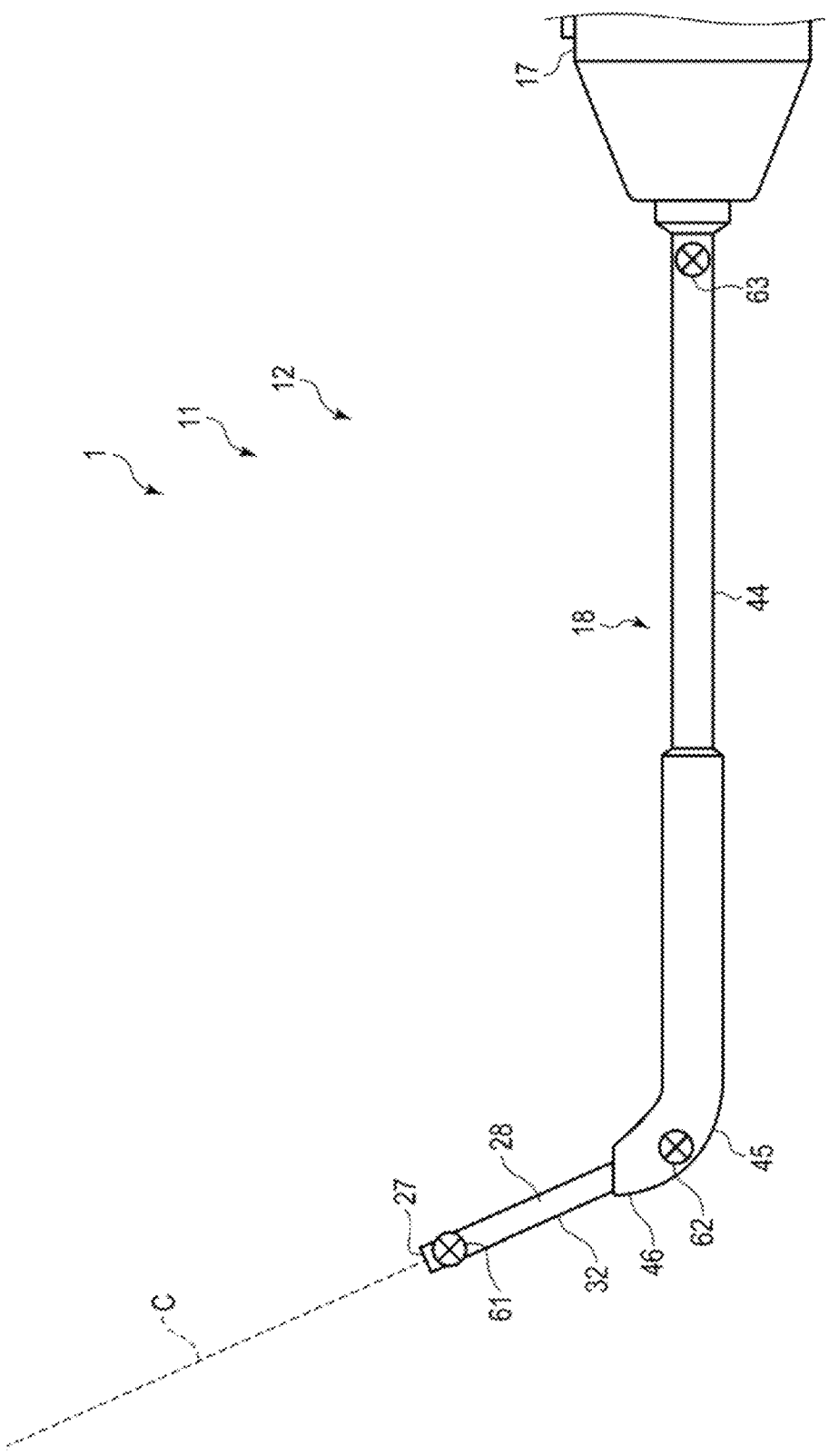
FIG. 15 is a schematic view illustrating the overall makeup of an image diagnosing system and an endoscopic system according to a third embodiment.

An endoscopic system 11 according to a third embodiment and an image diagnosing system 1 using the endoscopic system 11 according to the third embodiment will be described hereinafter with reference to FIG. 15. According to the third embodiment, the position where the first probe is disposed is different from the first embodiment, whereas other portions of the third embodiment are the same as those of the first embodiment. Hereinafter, those portions of the third embodiment which are different from the first embodiment will chiefly be described, and the illustration or description of those portions which are the same as those of the first embodiment will be omitted.

The first probe 61 is disposed on the distal-end structure portion, i.e., photodetector, 27 of the main endoscope body 21. The guide pipe 18 includes the second probe 62 that is disposed on the elbow portion 45, i.e., the shank 44, and the third probe 63 that is disposed on a base of the shank 44. Each of the first probe 61, the second probe 62, and the third probe 63 is in the form of a small piece of metal, for example. The position of each of the first probe 61, the second probe 62, and the third probe 63 in a three-dimensional space is detected by the navigation system 8 that is constructed as the magnetic sensor. The navigation system 8 may be constructed as an optical sensor.

The controller 13 stores information regarding a trajectory followed by the distal-end structure portion 27 when the main endoscope body 21 protrudes from the guide pipe, i.e., guide portion, 18. Therefore, the controller 13 does not erroneously recognize the posture of the insertion device 12 in a case where—it grasps the positions of the first through third probes 61 through 63 through the navigation system 8.

An observational method using the image diagnosing system 1 and the endoscopic system 11 according to the present embodiment will be described hereinafter with reference to FIG. 15, etc.

In the examination, the doctor who is the user can insert the main endoscope body 21 from a nostril 59 into the nasal cavity 55 of the medical examinee. When the endoscope 15 is the positional relationship illustrated in FIG. 5, i.e., when the endoscope 15 is the positional relationship in which the direction from the second probe 62 toward the first probe 61 is the same as the superior direction of the medical examinee, the user can carry out a calibration step for establishing the reference directions. The controller 13 can establish the first reference direction 71 and the second reference direction 72 in the same manner as with the first embodiment.

The present embodiment operates in substantially the same way as and offers substantially the same advantages as the first embodiment.

According to the present embodiment, the first probe 61 is disposed on the photodetector and the second probe 62 on the shank 44. With this arrangement, though the first probe 61 is disposed on the photodetector, since the process for indicating directions to the user in the image 16 displayed on the display device 14 is carried out, the user or the like is prevented from failing to know which direction in the actual space corresponds to the direction in which the user is seeing in the image 16. The endoscopic system 11 is thus rendered user-friendly.

The controller 13 has the information regarding the trajectory followed by the photodetector protruding from the protrusive portion 46. With this arrangement, even in case the main endoscope body 21 protrudes largely from the guide portion, it is possible to grasp the posture of the endoscope 15 appropriately. The controller 13 is thus prevented from erroneously recognizing the posture of the endoscope 15.

The certain embodiments have thus far been described in specific detail with reference to the drawings. The disclosed technology is not limited to the embodiments described hereinbefore, but the components may be modified into embodiments within the scope of the invention. The components described in the embodiments and modifications described hereinbefore may naturally be appropriately combined into one endoscopic system 11 and image diagnosing system 1.

In sum, the disclosed technology is directed to an endoscopic system comprises an endoscope having a shank and a photodetector engaged with one another and having an optical axis in a direction transverse to the shank. A display device for displaying an image acquired through the photodetector. A first probe is disposed in the endoscope on or around the optical axis at a position off the shank. A second probe is disposed in the endoscope at or near a position where the shank and the optical axis intersect with each other. A sensor for detecting the position of the first probe and the position of the second probe and a controller. The controller is configured to establish a first reference direction in an actual space. Next, to acquire a direction from the second probe toward the first probe or a direction from the first probe toward the second probe as a direction of the optical axis. Then, to perform a process for indicating the first reference direction to a user in the image displayed on the display device when an angle formed between the direction of the optical axis and the first reference direction exceeds a predetermined threshold value.

The controller establishes a second reference direction in the image and the process for indicating the first reference direction to the user includes a process for turning the image to bring the second reference direction into agreement with the first reference direction. The controller establishes a second reference direction in the image and the process for indicating the first reference direction to the user includes a process for displaying the second reference direction in the image. The endoscopic system further comprises a third probe disposed on the shank at a position off the position where the second probe is disposed and its position capable of being detected by the sensor. The second reference direction is established on a plane defined by the first probe, the second probe, and the third probe. The endoscope has a second sensor capable of detecting vertical directions, and the first reference direction is either an upward one of the vertical directions or a downward one of the vertical directions. The endoscope includes a tubular guide having the shank and a protrusive portion protruding from the shank in a direction transverse to the direction in which the shank extends and a main endoscope body having the photodetector. The main endoscope body is movable in the tubular guide in advanced and or retracted movement so as to project the photodetector from the protrusive portion. The main endoscope body is guided by the tubular guide when being in advanced and or retracted position. The first probe is disposed on the protrusive portion and the second probe is disposed on the shank. The first probe is disposed on the photodetector, and the second probe is disposed on the shank. The controller includes information regarding a trajectory followed by the photodetector protruding from the protrusive portion. The predetermined threshold value of the endoscopic system is 45°.

Another aspect of the disclosed technology is directed to an image diagnosing system having an endoscopic system comprises an endoscope having a shank and a photodetector engaged with one another and having an optical axis in a direction transverse to the shank. A display device for displaying an image acquired through the photodetector. A first probe is disposed in the endoscope on or around the optical axis at a position off the shank. A second probe is disposed in the endoscope at or near a position where the shank and the optical axis intersect with each other. A sensor for detecting the position of the first probe and the position of the second probe. A sectional image acquiring device for acquiring at least one sectional image of a medical examinee and a controller. The controller is configured to display a first image acquired by the endoscope and at least one second image acquired by the sectional image acquiring device, in an array on the display device, to establish a first reference direction in an actual space, to acquire a direction from the second probe toward the first probe or a direction from the first probe toward the second probe as a direction of the optical axis, and to perform a process for indicating the first reference direction to a user in the first image displayed on the display device when an angle formed between the direction of the optical axis and the first reference direction exceeds a predetermined threshold value.

A further aspect of the disclosed technology to a method of detecting an observational direction of an endoscope used in an endoscopic system. The method comprises detecting a position of a first probe disposed in the endoscope on or around an optical axis thereof at a position off a shank thereof. Next, detecting a position of a second probe disposed in the endoscope at or near a position where the shank and the optical axis intersect with each other. Then, establishing a first reference direction in an actual space and acquiring a direction from the second probe toward the first probe or a direction from the first probe toward the second probe as a direction of the optical axis. Finally, indicating the first reference direction to a user when an angle formed between the direction of the optical axis and the first reference direction exceeds a predetermined threshold value.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscopic system comprising:
   an endoscope having a shank and a photodetector engaged with one another and having an optical axis in a direction transverse to the shank;
   a display device for displaying an image acquired through the photodetector;
   a first probe disposed in the endoscope on or around the optical axis at a position off the shank;
   a second probe disposed in the endoscope at or near a position where the shank and the optical axis intersect with each other;
   a sensor for detecting the position of the first probe and the position of the second probe; and
   a controller wherein
   the controller configured to
      establish a first reference direction in an actual space,
      acquire a direction from the second probe toward the first probe or a direction from the first probe toward the second probe as a direction of the optical axis, and
      perform a process for indicating the first reference direction to a user in the image displayed on the display device when an angle formed between the direction of the optical axis and the first reference direction exceeds a predetermined threshold value.

2. The endoscopic system of claim 1, wherein
   the controller establishes a second reference direction in the image; and
   the process for indicating the first reference direction to the user includes a process for turning the image to bring the second reference direction into agreement with the first reference direction.

3. The endoscopic system of claim 1, wherein
   the controller establishes a second reference direction in the image; and
   the process for indicating the first reference direction to the user includes a process for displaying the second reference direction in the image.

4. The endoscopic system of claim 3 further comprising:
   a third probe disposed on the shank at a position off the position where the second probe is disposed, and said position capable of being detected by the sensor.

5. The endoscopic system of claim 4, wherein
   the second reference direction is established on a plane defined by the first probe, the second probe, and the third probe.

6. The endoscopic system of claim 1, wherein
   the endoscope has a second sensor capable of detecting vertical directions, and the first reference direction is either an upward one of the vertical directions or a downward one of the vertical directions.

7. The endoscopic system of claim 1, wherein
   the endoscope includes
      a tubular guide having the shank and a protrusive portion protruding from the shank in a direction transverse to the direction in which the shank extends; and
      a main endoscope body having the photodetector, the main endoscope body being movable in the tubular guide in advanced and or retracted movement so as to project the photodetector from the protrusive portion, the main endoscope body being guided by the tubular guide when being in advanced and or retracted positon.

8. The endoscopic system of claim 7, wherein
   the first probe is disposed on the protrusive portion; and
   the second probe is disposed on the shank.

9. The endoscopic system of claim 7, wherein
   the first probe is disposed on the photodetector; and
   the second probe is disposed on the shank.

10. The endoscopic system of claim 9, wherein
    the controller includes information regarding a trajectory followed by the photodetector protruding from the protrusive portion.

11. The endoscopic system of claim 1, wherein
    the predetermined threshold value is 45°.

12. An image diagnosing system having an endoscopic system comprising:
    an endoscope having a shank and a photodetector engaged with one another and having an optical axis in a direction transverse to the shank;
    a display device for displaying an image acquired through the photodetector;
    a first probe disposed in the endoscope on or around the optical axis at a position off the shank;
    a second probe disposed in the endoscope at or near a position where the shank and the optical axis intersect with each other;
    a sensor for detecting the position of the first probe and the position of the second probe;
    a sectional image acquiring device for acquiring at least one sectional image of a medical examinee; and
    a controller, wherein
    the controller configured to
       display a first image acquired by the endoscope and at least one second image acquired by the sectional image acquiring device, in an array on the display device,
       establish a first reference direction in an actual space,
       acquire a direction from the second probe toward the first probe or a direction from the first probe toward the second probe as a direction of the optical axis, and
       perform a process for indicating the first reference direction to a user in the first image displayed on the display device when an angle formed between the direction of the optical axis and the first reference direction exceeds a predetermined threshold value.

13. A method of detecting an observational direction of an endoscope used in an endoscopic system, the method comprising:
    detecting a position of a first probe disposed in the endoscope on or around an optical axis thereof at a position off a shank thereof;

detecting a position of a second probe disposed in the endoscope at or near a position where the shank and the optical axis intersect with each other;

establishing a first reference direction in an actual space;

acquiring a direction from the second probe toward the first probe or a direction from the first probe toward the second probe as a direction of the optical axis; and indicating the first reference direction to a user when an angle formed between the direction of the optical axis and the first reference direction exceeds a predetermined threshold value.

\* \* \* \* \*